United States Patent
Olsen

[11] Patent Number: 5,968,023
[45] Date of Patent: Oct. 19, 1999

[54] COLLECTING BAG FOR HUMAN BODY WASTES, PARTICULARLY A STOMA BAG, AND A CLOSURE CLIP FOR CLOSING A BAG

[75] Inventor: Hans Olsen, Hørsholm, Denmark

[73] Assignee: Coloplast A/S, Denmark

[21] Appl. No.: 08/860,219

[22] PCT Filed: Dec. 21, 1995

[86] PCT No.: PCT/DK95/00514

§ 371 Date: Jun. 23, 1997

§ 102(e) Date: Jun. 23, 1997

[87] PCT Pub. No.: WO96/19164

PCT Pub. Date: Jun. 27, 1996

[30] Foreign Application Priority Data

Dec. 22, 1994 [DK] Denmark .................................. 1467/94

[51] Int. Cl.[6] .................................................. A61F 5/44
[52] U.S. Cl. ..................... 604/334; 604/332; 24/30.5 R; 24/327
[58] Field of Search .................. 604/332–345; 24/30.5 R, 327

[56] References Cited

U.S. PATENT DOCUMENTS

| | | |
|---|---|---|
| 4,403,991 | 9/1983 | Hill . |
| 4,460,359 | 7/1984 | Fenton . |
| 4,465,486 | 8/1984 | Hill ........................................... 604/337 |
| 4,561,858 | 12/1985 | Allen, Jr. et al. ........................ 604/336 |
| 4,755,177 | 7/1988 | Hill .......................................... 604/336 |
| 4,834,730 | 5/1989 | Holtermann et al. . |
| 4,941,869 | 7/1990 | D'Amico ................................. 604/337 |
| 4,983,172 | 1/1991 | Steer et al. ............................... 604/332 |
| 4,988,343 | 1/1991 | Ballan . |
| 5,050,272 | 9/1991 | Robinson et al. ....................... 604/335 |
| 5,125,133 | 6/1992 | Morrison ................................. 604/335 |

FOREIGN PATENT DOCUMENTS 633704  12/1982  Switzerland .

*Primary Examiner*—John G. Weiss
*Assistant Examiner*—Dennis Ruhl
*Attorney, Agent, or Firm*—Ostrolenk, Faber, Gerb & Soffen, LLP

[57] ABSTRACT

A collecting bag for human body wastes, particularly a stoma bag, comprises a bag member formed by two oblong plastic film blanks with joined edges, of which one blank is designed with an inlet opening for connection to a body orifice, particularly a stoma. Between the edge sections of said joined film blanks a narrowed outlet opening is formed, which can be closed by means of a closure clip with a central part attached to one film blank and projecting end sections. At least the central part of the closure clip has along at least one of its longitudinal side edges a relatively soft, resilient edge zone.

11 Claims, 3 Drawing Sheets

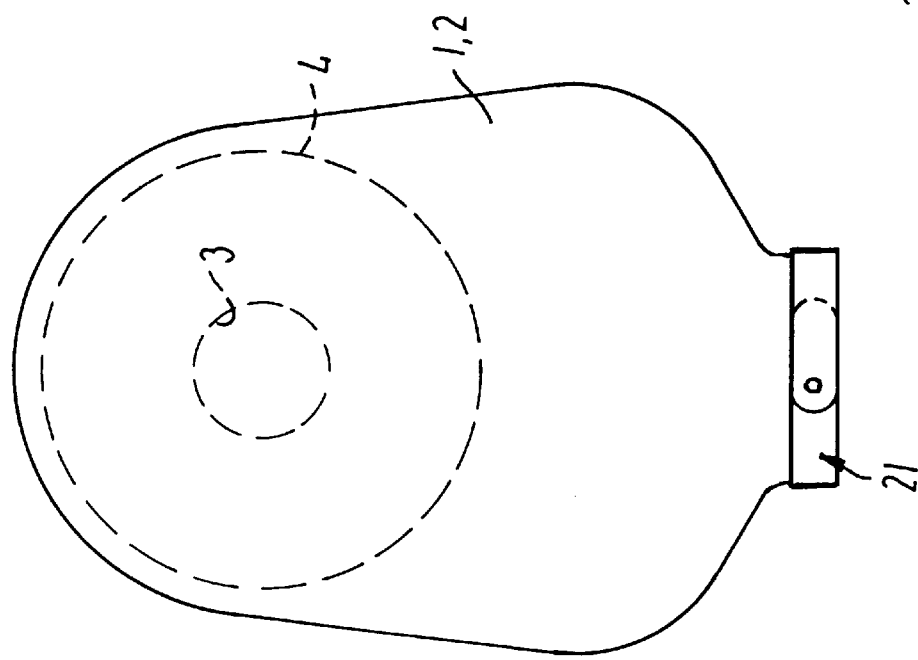
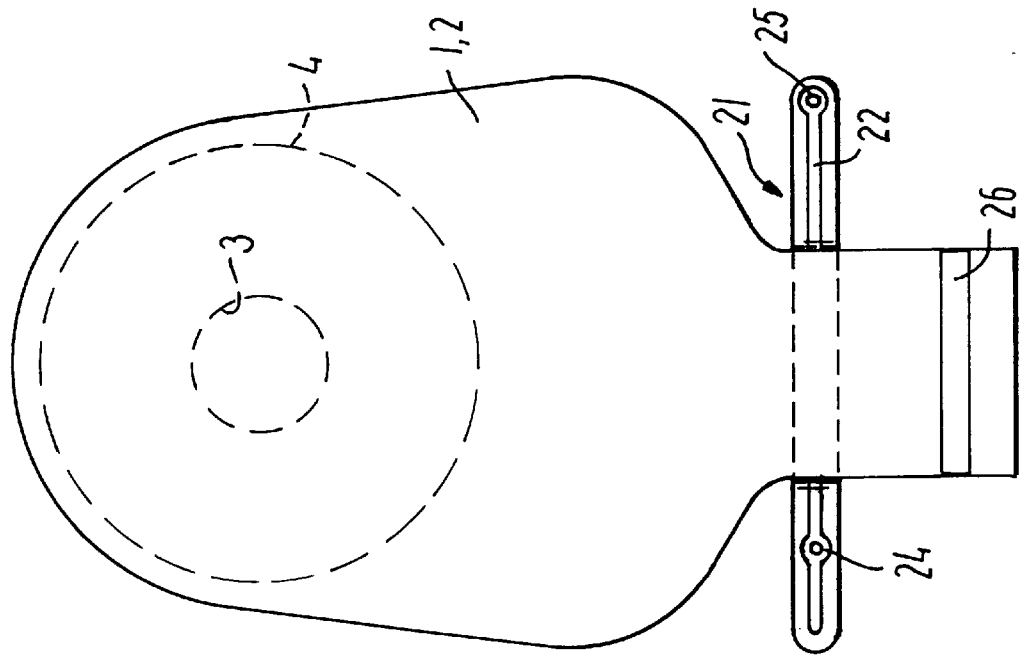

COLLECTING BAG FOR HUMAN BODY WASTES, PARTICULARLY A STOMA BAG, AND A CLOSURE CLIP FOR CLOSING A BAG

BACKGROUND OF THE INVENTION

The present invention relates to a collecting bag for human body wastes comprising a bag member formed by two oblong plastic film blanks with joined edges, of which one blank is designed with an inlet opening for connection to a body orifice, particularly a stoma, on which blank between its edge sections facing away from said port a narrowed outlet opening is formed which can be closed by means of a closure clip with a central part attached to one film blank and with projecting end sections, which are designed integrally with the central part via folding sections.

From U.S. Pat. Nos. 4,403,991 and 4,465,486, stoma bags of the type described above are known, with which fairly easy emptying and reclosing procedures of a stoma bag are achieved with a view to its reuse, which is particularly advantageous for ileostomy patients and colostomy patients with uncontrolled release of faeces of a more or less fluid consistency. Closure of the bag during use is achieved by folding the narrowed outlet end of the bag, near the opening so which the closure clip is attached, preferably on the outward-facing side, a couple of turns round the closure clip, after which the ends of the closure clip are folded round the folded outlet section.

U.S. Pat. No. 4,988,343 discloses a collecting bag and a closure clip which is enclosed in sheet material in order to keep the clip connected to the bag and secure that the clip is not contaminated by waste material.

Especially when the bag is filled almost to capacity, in which case the film material of the bag walls is subject to a considerable load, these known bags will entail a risk of a less than satisfactory sealing of the closure, for instance as a result of crease formation in the outlet section including the part rolled round the closure clip. If the bag is reused, this risk may increase as a result of the presence of faecal particles in the outlet opening.

Thus, the known bags entail a rather considerable risk of contamination and odour nuisances.

DESCRIPTION OF THE INVENTION

According to the invention, these inconveniences can be avoided by providing the closure clip at least along one of said longitudinal side edges with a relatively soft, resilient edge zone.

The design of the closure clip with such a soft, resilient edge zone along one or, preferably, both the longitudinal side edges means that the clip achieves a springy effect in said edge zones, providing a self-locking effect, while at the same time keeping the film material in the outlet section tight so that crease formation is essentially avoided, by which an improved sealing is achieved.

This springy effect is also an important advantage in connection with reuse of the bags, as it leads to compression of the film material in the outlet section round any remaining faecal particles.

In a preferred embodiment of the collecting bag according to he invention, the closure clip can also be provided with a relatively soft, resilient edge zone round said folding sections. This provides an improved comfort over the known designs described above, as the folding edges of the closure clip projecting from the bag cutlet section will feel relatively soft and thus considerably less discomfortable during use of the bag.

According to a further development the risk of contamination of the closure clip itself with faecal particles in connection with emptying the bag can be further reduced by attaching the closure clip removably to said one film blank at a distance from the mouth of the outlet opening, and by attaching removably to said one film blank, between the closure clip and the opening, a thin bar for rolling up the narrowed part of the bag outlet section. The narrowed outlet section is thus folded up round the thin band, by which procedure the folded-up part is completely surrounded by the closure clip, when the latter is subsequently closed.

The invention also relates to a closure clip for closing a bag by fastening it round its walls near an opening in the bag, which closure clip is designed with a central part and with end sections projecting from it which are designed integrally with the central part via folding sections.

The closure clip is characterized in that at least the central part along at least one of its longitudinal side edges has a relatively soft, resilient edge zone.

By designing the closure clip with such a soft and resilient edge zone along one or preferably both longitudinal side edges, the clip achieves a springy effect in said zones, which also applies to other forms of bags than stoma bags, eg, bags intended for relatively heavy and partially fluid contents, so that the a self-locking effect is achieved while at the same time the bag material is kept tight, thereby essentially preventing crease formation and resulting in an improved sealing effect.

BRIEF DESCRIPTION OF THE DRAWINGS

In the following the invention will be explained in further detail with reference to the schematic drawing, in which

FIGS. 4 and 5 show another embodiment of the collecting bag, shown with the outlet section open and closed, respectively; and FIG. 6 shows a cross-section of the closure clip in the embodiment shown in FIGS. 4 and 5.

EXAMPLES

Figure 1:
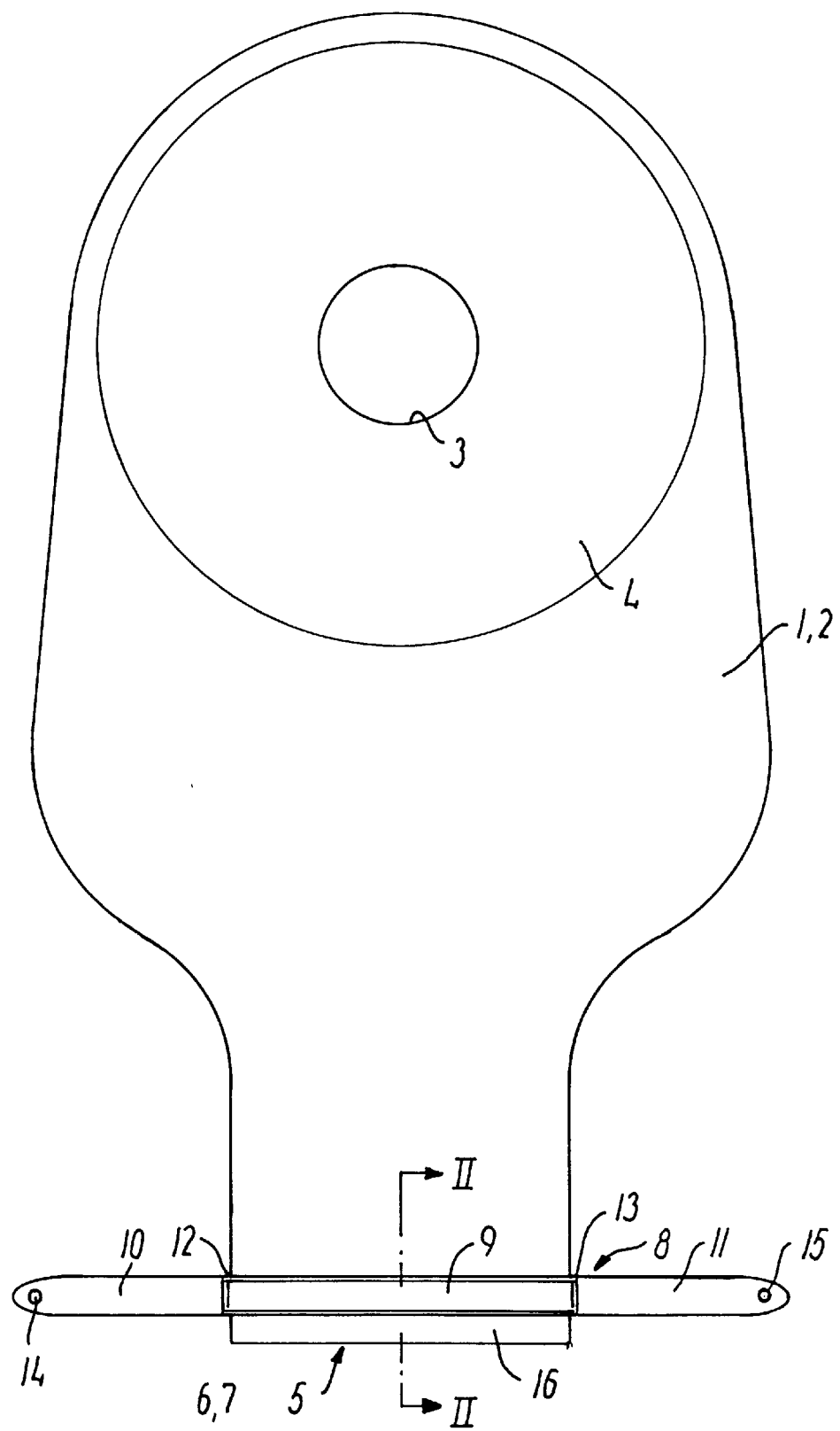
FIG. 1 shows an embodiment of a collecting bag according to the invention made like a stoma bag.
Figure 2:
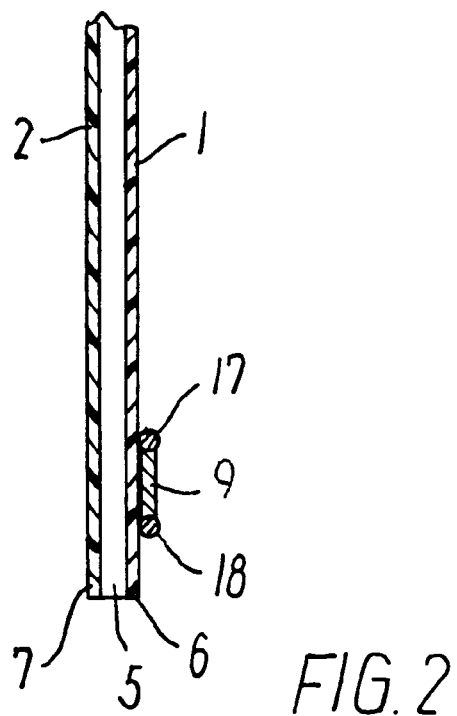
FIG. 2 shows a section of the bag outlet section perpendicular to the closure clip along the line II—II in FIG. 1.
Figure 3:
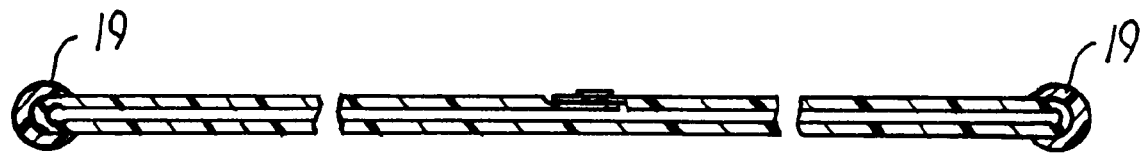
FIG. 3 shows a partially longitudinal section of the closure clip when closed.

FIG. 1 shows an embodiment of a collecting bag according to the invention designed as a stoma bag of a conventional design per se, with a bag member which, as shown in FIG. 2, is formed by two largely oblong plastic film blanks 1 and 2 with joined edges. In one film blank 1, forming the back side of the bag, an inlet opening 3 is formed, surrounded by a per se conventional adhesive plate 4 for fixing the bag on to the user's skin round the stoma.

At a distance from the inlet opening 3, the bag is designed with a narrowed outlet section with an outlet opening 5 formed between the end edge sections 6 and 7 of the film blanks 1 and 2. For closing the bag and on the outside of the back side film 1 facing towards the user near the outlet opening, a strip-shaped closure clip 8 is glued, comprising a central part 9 connected by adhesion with the bag film 1 and end sections 10 and 11, formed integrally with the central part 9 via folding sections 12 and 13. The end sections 10 and 11 are designed in a manner known per se with cooperating locking elements, eg, in the share of a hole 14 and a peg 15.

To close the bag, the edge zone 16 situated outside the central part of the closure clip at the outlet opening 5 is folded round the closure clip 8, and the latter is folded upwards a couple of turns, after which the end sections 10 and 11 are folded across the folded-up outlet section of the bag, preferably on the front side facing away from the user, and the closure clip is locked by means of the locking elements 14 and 15.

To improve the sealing of the closing mechanism, the central part of the closure clip 8 in the embodiment shown is designed with rather soft and resilient edge zones 17 and 18 along its longitudinal side edges, as shown in FIG. 2. The closure clip can be made by injection moulding of relatively hard plastic material, eg, polyethylene, whereas the soft, resilient edge zones 17 and 18 can be added by subsequently applying a moulded layer of a resilient polyurethane integral cellular plastic.

It is not absolutely necessary that both longitudinal edges of the central part of the closure clip 9 have a resilient edge zone, giving the clip a springy effect so that a self-locking effect is achieved. Thus it has turned out that an improved sealing can be achieved by applying the resilient integral cellular plastic 17 only on the longitudinal edge of the central part 9 facing away from the outlet opening 5.

In the embodiment shown, the closure clip 8 is also designed with soft, resilient edge zones 19 round the folding sections 12 and 13, so that these edge sections of the closure clip, projecting when the bag is closed, will feel relatively soft and thus less discomfortable.

FIGS. 4–6 show another embodiment, according to which the bag itself can be made in the same way as explained above, whereas, in its entirety, the closure clip 21 consists of a moulded two-component element with a core body 22 of semi-rigid plastic material, eg, nylon, surrounded by an outer layer 23 of resilient integral foam plastic, the core body, however, being extended to one side of the closure clip where it forms the locking elements 24 and 25.

The closure clip 21 is also situated at a larger distance from the outlet opening 5 than in the embodiment shown in FIGS. 1 and 2, whereas for rolling up the outlet section of the bag a thin bar 26 of a relatively hard plastic material like nylon is glued on to at least one film wall of the bag. When rolling up the outlet section of the bag by means of this band, the rolled-up section can, when the bag is closed, be placed so that it is completely surrounded by the closure clip 21 as shown in FIG. 5, providing a further improved sealing as a result of the springy effect of the closure clip.

In both embodiments the closure clip 8 or 21, respectively, can be glued on to the back side film 1 of the bag by means of an adhesive conventional per se, preferably of a kind that allows removing and replacing of the closure clip in a non-destructive manner.

Although the invention has been described above only with reference to stoma bags, it is in principle possible to apply it to other forms of collecting bags whether intended for human wastes, such as urinal bags or drainage bags for use in connection with surgery, or for other purposes involving collection of a relatively heavy body fluid content in the bag.

I claim:

1. A collecting bag for human body wastes comprising
   a bag member formed by two oblong plastic film blanks with joined edges,
   an inlet opening formed in one of said film blanks,
   connecting elements for connection of the bag to a body orifice, especially a stoma, surrounding said inlet opening, and
   a narrowed outlet opening formed between edge sections of said bag member facing away from said inlet opening,
   said outlet opening being closeable by means of a closure clip of a relatively hard plastic core body and having a central part attached to one of said film blanks and projecting end sections formed integrally with said central part and connected therewith by folding sections,
   at least said central part having at least one longitudinal side edge provided with a relatively soft, resilient zone formed by an outer coating of a resilient integral foam plastic.

2. A collecting bag as claimed in claim 1, wherein relatively soft, resilient edge zones are further provided around said folding sections.

3. A collecting bag as claimed in claim 1, wherein the closure clip is made entirely as a moulded two-component element, in which said core body is formed of a semi-rigid plastic material and is surrounded by a layer of said resilient integral foam plastic.

4. A collecting bag as claimed in claim 1, wherein said central part is removably attached to said one of said film blanks.

5. A collecting bag as claimed in claim 4, wherein said end sections are formed with mutually cooperating locking elements.

6. A collecting bag as claimed in claim 4, wherein said central part is attached to said one of said film blanks at a distance from said outlet opening and a thin bar is removably attached to said one film blank between the closure clip and the opening for rolling up a narrowed outlet section of the bag adjacent said outlet opening.

7. A closure clip adapted to close a bag member formed by two oblong plastic film blanks with joined edges and having an opening in one of said blanks, said closure clip comprising a relatively hard plastic core body having a central part and projecting end sections formed integrally with the central part and joined to the central part by folding sections, at least said central part having along at least one longitudinal side edge a relatively soft, resilient edge zone comprising an outer layer of resilient integral foam plastic providing a resilient response when said closure clip is folded and squeezed around the bag near said opening.

8. A closure clip as claimed in claim 7, wherein relatively soft, resilient edge zones are formed around said folding sections.

9. A closure clip as claimed in claim 7, consisting of a moulded two-component element with a core body of a semi-rigid plastic material surrounded by a layer of resilient integral foam plastic.

10. A closure clip as claimed in claim 7, wherein said central part is designed for removable attachment to a bag wall.

11. A closure clip as claimed in claim 10, wherein said end sections are formed with mutually cooperating locking elements.

* * * * *